(12) United States Patent
Trampota

(10) Patent No.: US 7,767,826 B2
(45) Date of Patent: Aug. 3, 2010

(54) PROCESS FOR THE SYNTHESIS OF L-(+)-ERGOTHIONEINE

(75) Inventor: Miroslav Trampota, West Orange, NJ (US)

(73) Assignee: Pharmatech International, Inc., Fairfield, NJ (US)

( * ) Notice: Subject to any disclaimer, the term of this patent is extended or adjusted under 35 U.S.C. 154(b) by 0 days.

(21) Appl. No.: 12/240,173

(22) Filed: Sep. 29, 2008

(65) Prior Publication Data

US 2009/0093642 A1   Apr. 9, 2009

Related U.S. Application Data

(60) Provisional application No. 60/977,906, filed on Oct. 5, 2007.

(51) Int. Cl.
*A61K 31/4172* (2006.01)
*C07D 233/42* (2006.01)

(52) U.S. Cl. .................. 548/316.4; 514/386

(58) Field of Classification Search .............. 548/316.4; 514/386

See application file for complete search history.

(56) References Cited

U.S. PATENT DOCUMENTS

| | | | |
|---|---|---|---|
| 4,265,892 A | 5/1981 | Kocsis et al. | |
| 5,438,151 A * | 8/1995 | Yadan et al. | 548/324.1 |
| 5,856,326 A | 1/1999 | Anthony et al. | |
| 5,879,444 A | 3/1999 | Badejo et al. | |
| 6,056,965 A | 5/2000 | Yadan et al. | |
| 6,103,746 A | 8/2000 | Yarosh | |
| 6,248,755 B1 | 6/2001 | Chapman et al. | |
| 6,326,034 B1 | 12/2001 | Mirsky et al. | |
| 6,451,771 B1 | 9/2002 | Henderson et al. | |
| 6,479,533 B1 | 11/2002 | Yarosh | |
| 6,555,141 B1 | 4/2003 | Corson et al. | |
| 6,635,802 B1 | 10/2003 | Piedrahita et al. | |
| 7,022,317 B2 | 4/2006 | Erdelmeier et al. | |
| 7,122,211 B2 | 10/2006 | Jensen et al. | |
| 7,138,249 B2 | 11/2006 | Hinuma et al. | |
| 2004/0019031 A1 | 1/2004 | Crapo et al. | |
| 2005/0202507 A1 | 9/2005 | Landis et al. | |

FOREIGN PATENT DOCUMENTS

JP    2006160748 A    6/2006

* cited by examiner

*Primary Examiner*—Joseph K. McKane
*Assistant Examiner*—Janet L Coppins
(74) *Attorney, Agent, or Firm*—St. Onge Steward Johnston & Reens LLC

(57) ABSTRACT

This invention relates to a novel process for the preparation of optically pure L-(+)-ergothioneine. The process for the chemical synthesis of L-ergothioneine comprises steps which consist of reacting L-histidine alkyl ester with an acid halide, chloroformate or pyrocarbonate in the presence of a base, hydrolysis of the alkyl-(S,Z)-2,4,5-triamidopent-4-enoate to obtain a (S)-alkyl 2,5-diamido-4-oxopentanoate, acid catalyzed hydrolysis of the (S)-alkyl 2,5-diamido-4-oxopentanoate followed by reaction with a metal thiocyanate to obtain the thiohistidine, protection of the sulfur of thiohistidine as the tert-butyl thioether, dialkylation of the primary amine to obtain a tertiary amine, quaternization of the tertiary amine, and removal of the protecting group to obtain the desired (S)-3-(2-mercapto-1H-imidazol-5-yl)-2-(trialkylammonio)propanoate (I). This process affords a better yield and is capable of practical application at large scale.

22 Claims, No Drawings

PROCESS FOR THE SYNTHESIS OF L-(+)-ERGOTHIONEINE

CROSS-REFERENCE TO RELATED APPLICATIONS

This application claims priority benefits of the U.S. Provisional application No. 60/977,906 filed on Oct. 5, 2007.

FIELD OF THE INVENTION

This invention relates to a novel process for the preparation of optically pure L-(+)-ergothioneine.

BACKGROUND OF THE INVENTION

Ergothioneine, shown in Formula 1, was originally described as a component of ergot fungus (Eagles, B. A., *J. Am. Chem. Soc'y* (1928) 50 pp. 1386-87) which did not possess ergot alkaloid activity. This compound was identical with a thiol previously known to occur in human and animal blood (see for example Eagles, B. A. and Johnson, T. B., *J. Am. Chem. Soc'y* 49 (1927) pp. 575-80). Ergothioneine was early recognized to be present in normal human blood in both health and disease (Touster, O. and M. C. Yarbro, *J. Lab. & Clinical Med.* 39(5) (1952) pp. 720-24), and was found to reside exclusively in the erythrocytes (Rae, C. D. et al., *Magnetic Resonance in Med.* 29(6) (1993) pp. 826-29). Ergothioneine was found to be present even in the central nervous system (Briggs, I., *J. of Neurochem.* 19(1) (1972) pp. 27-35) and at especially high levels in seminal fluid (Mann, T. and E. Leone, *Biochem. J.* 53(1) (1953) pp. 140-8), and also in the cornea (Shires, T. K. et al., *Toxicology, Endocrinology* 117(1) (1997) pp. 117-20).

Interestingly, ergothioneine is biosynthesized exclusively by fungi and mycobacteria. In plants, ergothioneine is assimilated by the roots after fungal synthesis inside the conidia. In man, it is assimilated solely through food. Ergothioneine is specifically taken up in the erythrocytes by a specific transporter (Gründemann, D. et al., *Proceedings Nat'l Acad. Sci. of U.S.* 102(14) (2005) pp. 5256-61) and remains in them for a long period, thus giving ergothioneine a long biological half-life (Wolf, G. et al., *Biochimica et Biophysica Acta* 54 (1961) pp. 287-93).

Although there has been recent controversy as to the precise role of ergothioneine in the human and animal body (Brummel, M. C., *Med. Hypotheses* 18(4) (1985) pp. 351-70), it was hypothesized and subsequently demonstrated in a wide variety of in vivo and in vitro models that the compound possesses potent antioxidant properties (Akanmu, D., et al., *Archives of Biochem. & Biophysics,* 288(1) (1991) pp. 10-16; Arduini, A. et al., *Archives of Biochem. & Biophysics* 281(1) (1990) pp. 41-3; Aruoma, O. I. et al., *Food & Chem. Toxicology* 37(11) (1999) pp. 1043-53; Bedirli, A., et al., *J. Surgical Research* 122 (2004) pp. 96-102; Hartman, P. E., *Methods in Enzymology* 186 (1990) pp. 310-18.; Hartman, Z. and Hartman, P. E., *Envtl. & Molecular Mutagenesis* 10 (1987) pp. 3-15.; Jang, J. H. et al., *Free Radical Biology & Med.* 36 (2004) pp. 288-99.; Moncaster, J. A. et al., *Neuroscience Letters* 328 (2004) pp. 55-59.; Obayashi, K. et al., *J. Cosmetic Sci.* 56 (2005) pp. 17-27; and references therein which are incorporated herein by reference). Free radicals derived from endogenous and exogenous thiol (sulphur)-containing compounds are involved in a number of important biological processes, such as the protection of living systems subjected to ionizing radiation or other sources of free-radical damage. Thiol or thione functions can be associated with the imidazole ring leading to the mercaptoimidazole ergothioneine(I), which exerts chemoprotection against oxidative stress and carcinogenesis.

Dietary ergothioneine, a compound of plant origin, is assimilated and conserved by mammals (see references supra). In aqueous solution, ergothioneine has a predominantly thione rather than tautomeric thiol structure. It is considered to be a natural chemoprotector against oxidation including lipid peroxidation. Ergothioneine deactivates singlet oxygen at a higher rate constant than is observed for simple thiols, including glutathione. It diminishes the mutagenicity of cumene and t-butylhydroperoxides in *Salmonella* bacteria (see references supra).

SUMMARY OF THE INVENTION

The present invention specifically relates to processes for the preparation of the compound of Formula (I):

Formula (I)

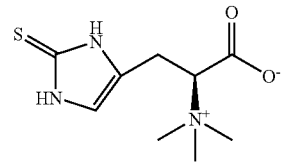

Formula 1 is known as ergothioneine, (α-S)-α-carboxy-2,3-dihydro-N,N,N-trimethyl-2-thioxo-1H-imidazole-4-ethanaminium inner salt, [1-carboxy-2-[2-mercaptoimidazol-4-yl]ethyl]trimethylammonium hydroxide inner salt, or simply thioneine (CAS 497-30-3), and also the intermediates which are used therein. It should further be recognized that in solution ergothioneine exists as two tautomeric structures as illustrated below:

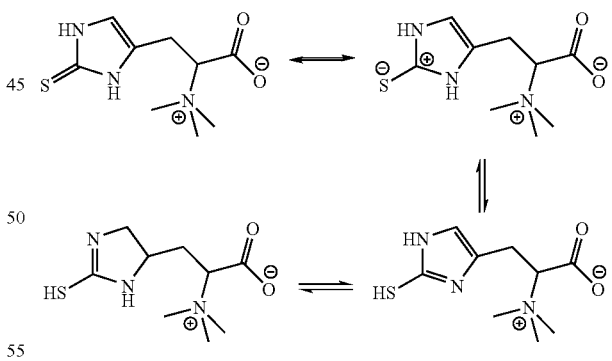

More specifically, the present invention concerns a process for the preparation of ergothioneine that is more efficient than those known in the prior art and which, surprisingly, can directly provide ergothioneine of clinical quality standard, thus obviating the need for additional steps of purification. In this context, ergothioneine of clinical standard means material of sufficient purity for administration to humans. Ergothioneine is useful as it possesses potent pharmacological activity as an antioxidant and protectant from damage by free radicals both in vitro in tissue culture as well as in vivo in animals and man.

A closely related system to ergothioneine is known as ovothiol. In ovothiol, the sulfur is present at a different position than it is in ergothioneine. Illustrated below are ovothiol A, B, and C which differ by their state of N-methylation. Ovothiols have similar antioxidant properties to ergothioneine.

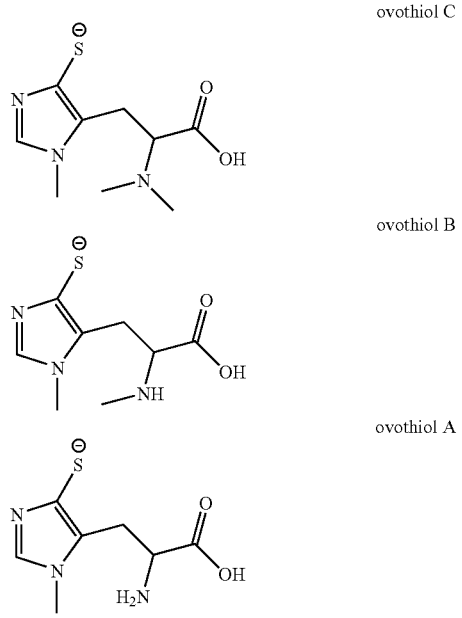

ovothiol C ovothiol B ovothiol A

The use of ergothioneine has been claimed as skin toner additive (U.S. Pat. No. 7,122,211 (filed Oct. 17, 2006)), as a photoprotective agent for human skin (U.S. Pat. No. 7,022,317 (filed Apr. 4, 2006)), for use in cell culture (U.S. Pat. No. 6,635,802 (filed Oct. 21, 2003)), for the amelioration of liver disease by virtue of its antioxidant activity (U.S. Pat. No. 6,555,141 (filed Apr. 29, 2003)), for preventing mitochondrially-mediated cell death (apoptosis) by antioxidant activity (U.S. Pat. No. 6,479,533 t (filed Nov. 12, 2002); U.S. Pat. No. 6,103,746 (filed Aug. 15, 2000)), for repair of skin connective tissue damage through its antioxidant activity (U.S. Pat. No. 6,451,771 (filed Sep. 17, 2002)), and for other pharmaceutical antioxidant uses (U.S. Pat. No. 6,326,034 (filed Dec. 4, 2001); U.S. Pat. No. 6,056,965 (filed May 2, 2000)). Unfortunately, the wide use of ergothioneine for these multiple indications has been greatly hindered by its very high cost (see e.g. Sigma-Aldrich Catalogue, 2007) which has made its use in such products described supra uneconomical. This fundamental problem is due to the fact that the synthesis of ergothioneine on even a moderate scale has remained difficult, and suffers from multiple technical problems.

The preparation of ergothioneine by several different processes has been described in the prior art (Ashley, J. N. and Harrington, C. R., *J. Chem. Soc.* (1930) pp. 2586-2590; Harrington, C. R. and Overhoff, J. *J. Chem. Soc.* (1933) pp. 338-344; Heath, H. et al., *Nature* 166 (1950) p. 106.; Xu, J. and Yadan, J. C., *J. Org. Chem.* 60 (1995) pp. 6296-6301 and references therein which are incorporated herein by reference; see also U.S. Pat. No. 5,438,151 (filed Aug. 1, 1995); Japanese Pat. App. 2006160748 (filed Jun. 22, 2006)). However, all these procedures suffer from one or another serious defect which hinders production of adequate amounts of pure L-(+)-ergothioneine. Efforts to repeat the procedures using the methods in the prior art led to inconsistent yields of ergothioneine. Moreover, the general processes disclosed in the art for the preparation of ergothioneine result in relatively low and inconsistent yields of the desired product.

To employ ergothioneine in applications such as have been described supra, it is necessary to have methods available which will allow the production of ergothioneine in an acceptable yield and of sufficient purity for pharmaceutical and nutraceutical applications. Specifically, the early syntheses of ergothioneine (see Ashley, Harrington, and Heath articles cited above) give overall stated yields of less than 20%, and in the hands of one normally skilled in the art such as the present investigators, were not reproducible. In contrast to the previously known processes, the present invention provides effective methodology for the preparation of ergothioneine in a relatively higher yield.

The most recently disclosed synthesis (Xu article cited above; U.S. Pat. No. 5,438,151 (filed Aug. 1, 1995)) although reproducible, requires the use of toxic reagents, such as thiophosgene and phenol, to prepare the phenyl chlorothionoformate mandatory for the described reactions (see footnote 30 in Xu article cited above). Thiophosgene is hazardous to handle and the subsequently formed phenol is a serious disposal problem. It also leads to phenolic contaminants which are difficult to remove from the reaction process. Final purification using this synthesis is, therefore, problematic and chromatographic separations are required. Because of these issues, the stated overall yield of 34%, is, in the hands of one normally skilled in the art, difficult to reproduce.

A key step in the reaction sequence involves the Bamberger reaction illustrated below:

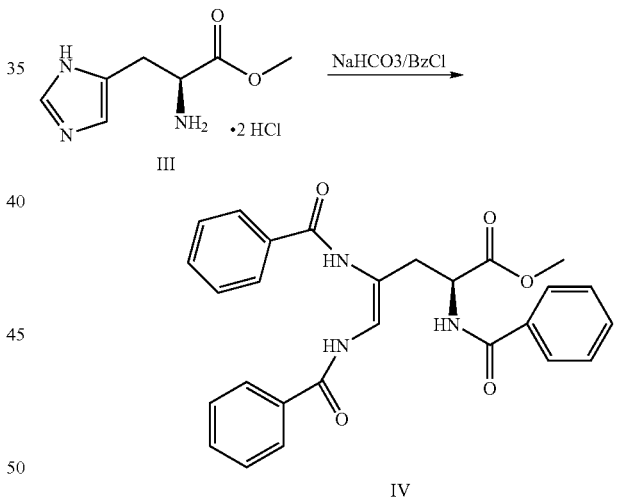

The Bamberger reaction (Bamberger, E. and Berle, B., *Leibigs Annalen der Chemie* (1893) pp. 342-63; Altman, J. and Wilchek, M., *Leibigs Annalen der Chemie* (1989) pp. 493-95), is well known in the prior art but conditions and yields have been variable and thus, the reaction has not been commonly employed in practical synthetic processes. Various chloroformates (Pratt, R. F. and Kraus, K. K., *Tetrahedron Letters* 22 (1981) pp. 2431-34) and pyrocarbonates (Grace, M. E. et al., *J. Am. Chem. Soc.* 102 (1980) pp. 6784-89; Altman, J. et al., *Chem. Commc'ns* (1985) pp. 1133-1134) can be employed in the reaction, but the precise conditions and retention of optical activity versus racemization is not well defined. However, one report indicated that the transformation of intermediate III to intermediate IV could be carried out without loss of chirality in good yield (Altman, J et al., *Leibigs Annalen der Chemie* (1990) pp. 339-43) which encouraged the inventors of the present invention to employ this basic approach. Heath et al. (supra) had been unable to preserve chirality because deformylation was carried out in boiling ethanol instead of the milder conditions employed by Altman et al.

In the most preferred embodiment of the invention, the Bamberger cleavage is performed in a tetrahydrofuran-water mixture. Other solvents can also be used that are at least partially miscible with water and will not react at an appreciable rate with benzoyl chloride. These solvents include 2-methyltetrahydrofuran, dioxane, methyl ethyl ketone, acetone, dimethylformamide, dimethylsulfoxide, diglyme, (bis)-methoxymethyl ether, (bis)-2-ethoxyethyl ether, and the like.

A key distinction of the present synthesis is the protection of the sulfur atom with the readily removable t-butyl group late in the reaction sequence. Other protecting groups can be employed such as trityl, diphenhydryl, or others well known in the art (for a comprehensive listing of protecting groups for sulfur see Peter G. M. Wuts and Theodora W. Greene, *Greene's Protective Groups in Organic Synthesis* (4th Ed. Wiley-VCH 2006)).

Another critical step of the present synthesis of ergothioneine is the transformation of VI to VIII, shown below in Reaction Scheme (I). Most approaches to alkylation in the prior art resulted in racemization and suffered from low yields (Heath et al. cited above). Use of DMF acetals was attractive (Alves et al., *European J. Org. Chem.* 29 (2007) pp. 4881-87) but typically resulted in ring alkylation of the imidazole in addition to alkylation of the desired amino nitrogen. The Xu synthesis employed demethylation prior to thionation of the imidazole ring, which is impossible in the present synthetic sequence. Such vigorous methods even with the t-butyl protected sulfur result in some degree of racemization.

The reductive amination is step illustrated below:

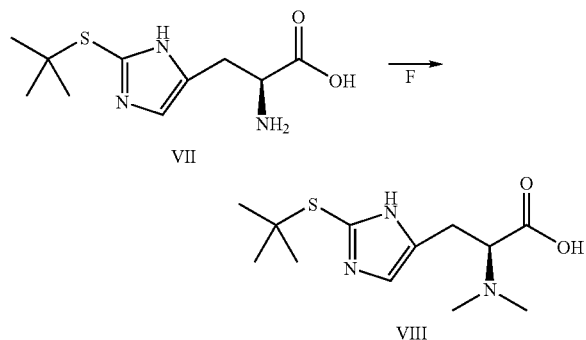

Many methods of reductive amination are well known in the prior art. Suitable imine reducing agents include in a non-limiting manner formic acid, borohydrides, aluminum hydrides and transition metals. Specific examples of such imine reducing agents include without limitation: lithium aluminum hydride, diisobutyl aluminum hydride, iron pentacarbonyl, zinc with hydrochloric acid, alcoholic potassium hydroxide, lithium cyanoborohydride, palladium on carbon with hydrogen, sodium cyanoborohydride, sodium triacetoxyborohydride, sodium borohydride, and pyridine-borane complex.

Applicant unexpectedly found that sodium triacetoxyborohydride below room temperature resulted in high product yield without any racemized product present, which represents a shorter, simpler and higher yield than the processes known in the art. The preparation of sodium triacetoxyborohydride in benzene from sodium borohydride and acetic acid is described by Evans et al. (*J. Am. Chem. Soc.* 110 (1988) pp. 3560-78), and it is also available commercially (Sigma Aldrich Catalog, 2007). Reductive amination procedures using sodium triacetoxyborohydride are known (See e.g. Abdel-Magid, A. F. et al., *J. Org. Chem.* 61 (1996) pp. 3849-62). The present invention employs commercially avialable sodium triacetoxyborohydride as well as sodium triacetoxyborohydride made by adding acetic acid to sodium borohydride. Sodium triacetoxyborohydride is commonly used at room temperature for reductive alkylation (See U.S. Pat. No. 6,248,755 col. 194 (filed Apr. 4, 2000); U.S. Pat. No. 5,856,326 col. 76-98 (filed Mar. 1, 1996); and Abdel-Magid reference cited above).

The step involving the formation of the quaternary salt is illustrated below:

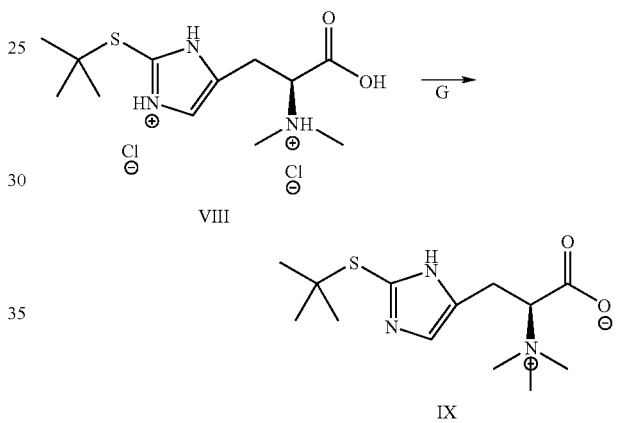

Quaternarization can be performed readily with any alkyl iodide. If analogues of ergothioneine are desired in which the alkyl nitrogen contains different alkyl groups, then methyl is required. Other methylating agents could be utilized for this step, including without limitation methyl bromide, methyl chloride, dimethyl sulfate, trimethyloxonium tetrafluoroborate, methyl methanesulfonate, and methyl trifluoromethanesulfonate. A suitable aprotic solvent for this step includes: benzene, cyclohexane, pentane, hexane, toluene, cycloheptane, methylcyclohexane, heptane, ethylbenzene, m-, o-, or p-xylene, octane, indane, nonane, naphthalene, tetramethylurea, nitromethane, nitrobenzene, dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether, carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, or fluorobenzene. Methanol is the preferred solvent.

The final deprotection step is illustrated below:

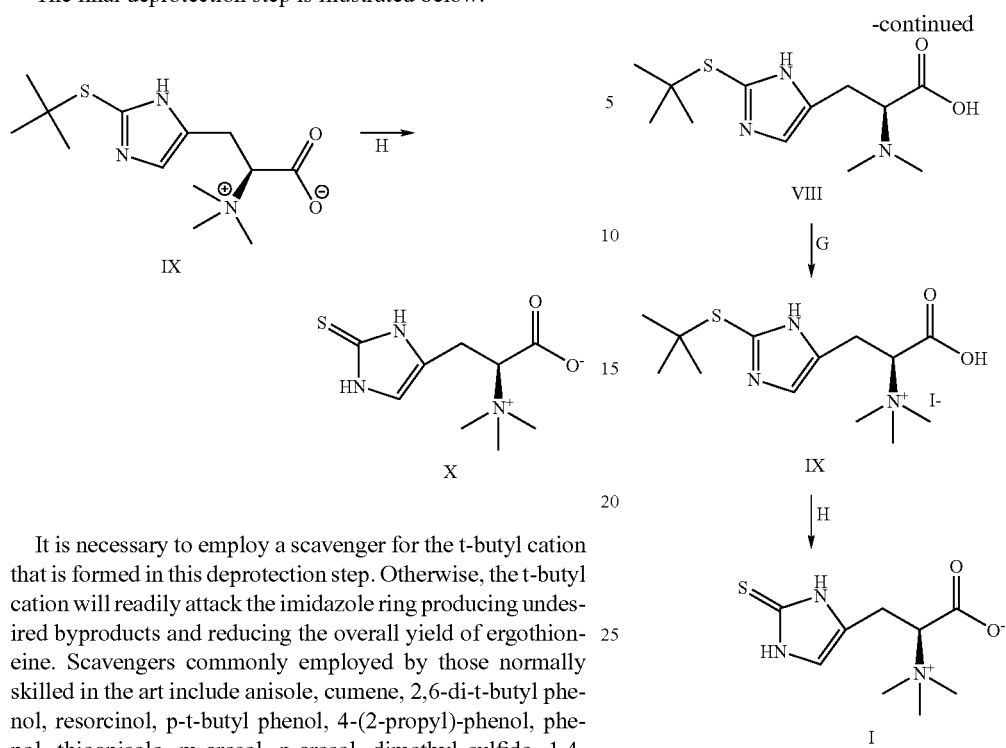

It is necessary to employ a scavenger for the t-butyl cation that is formed in this deprotection step. Otherwise, the t-butyl cation will readily attack the imidazole ring producing undesired byproducts and reducing the overall yield of ergothioneine. Scavengers commonly employed by those normally skilled in the art include anisole, cumene, 2,6-di-t-butyl phenol, resorcinol, p-t-butyl phenol, 4-(2-propyl)-phenol, phenol, thioanisole, m-cresol, p-cresol, dimethyl sulfide, 1,4-butanedithiol, 1,2-ethanedithiol, 2-mercaptoethanol, bis(hydroxymethyl)disulfide, D-penecillamine, cysteine, and the like (See U.S. Pat. No. 7,138,249 col. 8-9 (filed Nov. 21, 2006)). Of these, the most preferred is 2-mercaptopropionic acid.

The compound of formula (I) may be obtained by the following route, depicted in Reaction Scheme (I):

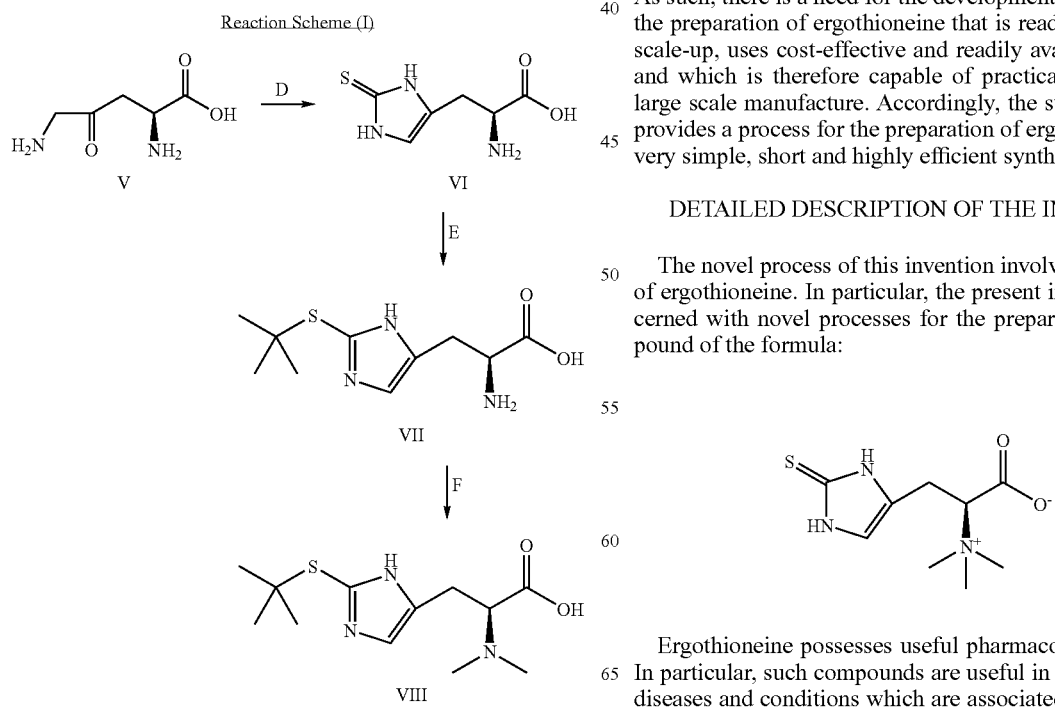

In accordance with the present invention, the use of the presently-disclosed process results in a more pure ergothioneine without need for chromatographic separation with higher yields of the product and lower amounts of byproducts. It will be appreciated that ergothioneine is important and useful as it possesses potent pharmacological activity as an antioxidant and protectant from damage by free radicals both in vitro in tissue culture as well as in vivo in animals and man. As such, there is a need for the development of a process for the preparation of ergothioneine that is readily amenable to scale-up, uses cost-effective and readily available reagents, and which is therefore capable of practical application to large scale manufacture. Accordingly, the subject invention provides a process for the preparation of ergothioneine via a very simple, short and highly efficient synthesis.

DETAILED DESCRIPTION OF THE INVENTION

The novel process of this invention involves the synthesis of ergothioneine. In particular, the present invention is concerned with novel processes for the preparation of a compound of the formula:

Ergothioneine possesses useful pharmacological activity. In particular, such compounds are useful in the treatment of diseases and conditions which are associated with oxidative damage and damage by free radicals in man and in animals.

As used herein the term "alkyl" refers to a straight or branched chain hydrocarbon group containing no unsaturation and having from 1 to 8 carbon atoms. Examples of alkyl groups are methyl, ethyl, propyl, isopropyl, neopentyl, tert-pentyl, hexyl, pentyl, and octyl, and the like. Examples of the alkyl group represented are n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, 1-methyl-1-propylbutyl and the like.

As used herein the term "Cycloalkyl" refers to a species of alkyl containing from 3 to 15 carbon atoms, without alternating or resonating double bonds between carbon atoms. It may contain from 1 to 4 rings which are fused.

As used herein the term "alkenyl" refers to a straight, branched or cyclic hydrocarbon radical containing from 2 to 10 carbon atoms and at least one carbon to carbon double bond. Preferred alkenyl groups include ethenyl, propenyl, and butenyl.

As used herein the term "alkynyl" refers to a straight or branched hydrocarbon radical containing from 2 to 10 carbon atoms and at least one carbon-to-carbon triple bond. Preferred alkynyl groups include ethynyl, propynyl and butynyl.

As used herein the term "cycloalkenyl" refers to a hydrocarbon group having one carbocyclic ring of 4 to 9 carbon atoms and one carbon-to-carbon double bond. Examples of cycloalkenyl groups are cyclopropyl, cyclobutenyl, cyclopentenyl, and cyclohexenyl. Examples of the haloalkyl group are 3-fluoropropyl, 2,2,3,3,3-pentafluoropropyl, 2-chloro-1-methylpropyl, 3-chloropropyl, 2-chloropropyl, 2,3-dichloropropyl, 3-bromopropyl, 2-bromopropyl, 3-iodopropyl, 4-fluorobutyl, 3,3,4,4,4-pentafluoro-2-butyl, 4-chlorobutyl, 3-chlorobutyl, 2,3,4-trichlorobutyl, 4-bromobutyl, 3-bromobutyl, 4-iodobutyl, 5-fluoropentyl, 5-chloropentyl, 5-bromopentyl, 6-fluorohexyl, 6-chlorohexyl, 6-bromohexyl, 7-fluoroheptyl, 7-bromoheptyl, 8-fluorooctyl, 8-bromooctyl and the like. Examples of the cyanoalkyl group are cyanomethyl, 2-cyanoethyl, 3-cyanopropyl, 4-cyanobutyl, and the like.

As used herein the term "aryl" refers to aromatic rings e.g., phenyl, substituted phenyl and the like, as well as rings which are fused, e.g., naphthyl, phenanthrenyl and the like. An aryl group thus contains at least one ring having at least 5 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl. Aryl shall further include optionally substituted aryl, typically but not limited to one or a plurality of chloro, bromo, fluoro, methoxy, ethoxy, propyloxy, phenoxy, substitute aryloxy, or butoxy, alkyl, aralkyl, cycloalkyl, alkenyl, alkynyl, cycloalkenyl, nitro, hydroxy, or trifluoromethyl, difluoromethyl, fluoromethyl, trifluoromethoxy, trifluoroethoxy, trifluoromethylthio, trifluoroethylthio, difluoromethylthio, fluoromethylthio, oximino, and sulfonamide groups. Specific examples of aryl groups which may have substituents are phenyl, 4-methylphenyl, 4-chlorophenyl, 2,3-dimethylphenyl, 3,5-dimethylphenyl, 2,6-dimethylphenyl, 4-methoxyphenyl, 3-phenoxyphenyl, 4-phenylphenyl, 4-(2-chlorophenyl)phenyl, 4-(3-isoxazolylphenyl)phenyl, 3-benzylphenyl, 2-pyridylmethylphenyl groups and the like. Aryl further refers to heteroaryl, which is a monocyclic aromatic hydrocarbon group having 5 or 6 ring atoms, or a polycyclic aromatic group having 8 to 16 atoms, containing at least one heteroatom, O, S, S(O), $SO_2$ or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole and the like.

As used herein the term "aralkyl" is intended to mean an aryl or heteroaralkyl or heteroaromatic moiety, as defined above, attached through a C1-6 alkyl linker, where alkyl is defined above. Examples of aralkyls include, but are not limited to, benzyl, naphtylmethyl, phenylpropyl, 2-pyridylmethyl, 2-imidazolylethyl, 2-quinolinylmethy, 2-imidazolylmethyl and the like.

Examples of polycyclic heteroaromatics include benzopyrans, benzofurans, benzopyrroles, benzimidazoles, benzothiazoles, quinolines, purines, isoquinolines, benzopyrimidines, dibenzofurans, dibenzothiophenes, 1,8-naphthosultams.

As used herein the term "heterocycle" (heterocyclyl) refers to a 5-16 membered cycloalkyl group (nonaromatic) with 1-4 rings, in which one of the carbon atoms in the ring is replaced by a heteroatom selected from O, S or N, and in which up to three additional carbon atoms may be replaced by heteroatoms. Examples include pyridine, thiophene, pyrazine, pyrrolidine, pyran, dioxane, dithiane, thiazole, thiadiazoles, tetrazole, selenazoles, and the like.

As used herein the term "heteroatom" means O, S, S(O), S(O)2 or N, selected on an independent basis Any molecular entity of the present invention may be used in the form of a pharmaceutically acceptable salt. Reaction sequences typically illustrate hydrochloride salts. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, benzoic acid, naphthalene sulfonic acid, sulfanilic acid, pamoic acid, naphthenic acid or the like. Suitable bases capable of forming pharmaceutically acceptable salts with molecular entities of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

As used herein, an alkali metal is defined as sodium, potassium, cesium, rubidium, calcium, strontium, or barium.

As use herein the term "borohydride" indicates either an alkali metal borohydride, an alkali metal cyanoborohydride, an alkali metal trialkoxy borohydride, an alkali metal tri(alkanoic acid ester) borohydride, an alkali metal trialkyl borohydride, copper(I) borohydride, Cobalt(III) borohydride, Iron (II) borohydride, Iron (III) borohydride, a titanium alkoxyborohydride, or a zirconium alkoxyborohydride.

The compounds prepared by the invention process may have one or more chiral centers and may exist in, and be used or isolated in, optically active and racemic forms. It is to be understood that the processes of the present invention can give rise to any racemic or optically-active forms, or mixtures thereof. It is to be further understood that the products of the invention process can be isolated as racemic, enantiomeric, or diastereomeric forms, or mixtures thereof. Purification and characterization procedures for such products are known to those of ordinary skill in the art, and include recrystallization techniques, as well as chiral chromatographic separation procedures and other methods.

The present invention is directed to processes for the preparation of ergothioneine of formula (I). The general process for the preparation of ergothioneine is as follows in Reaction Scheme (II):

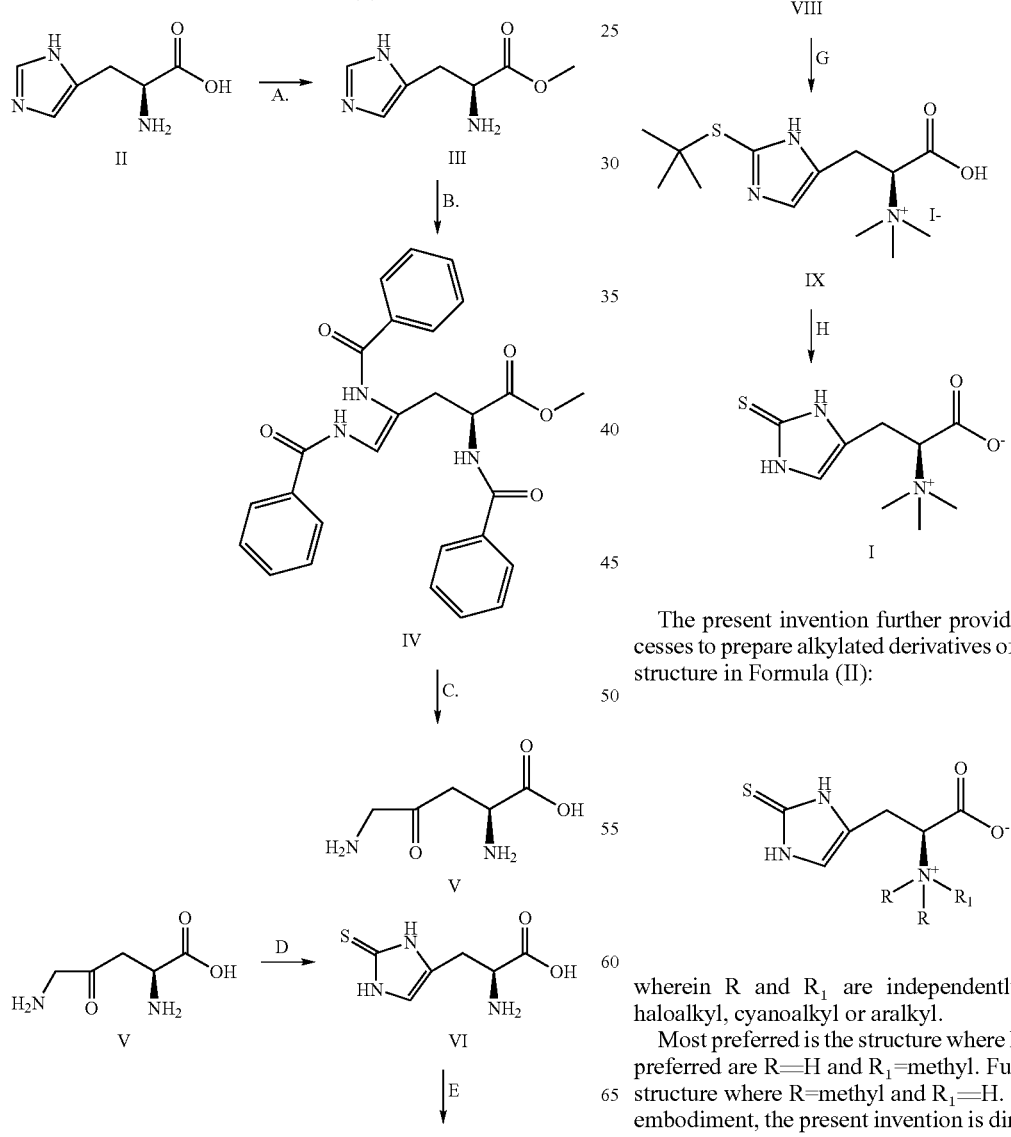

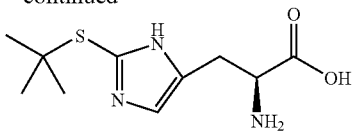

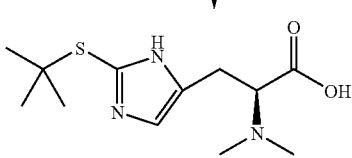

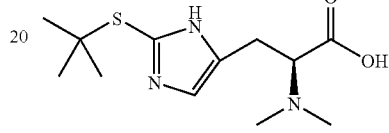

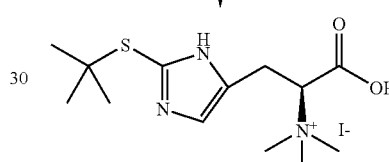

The present invention further provides methods and processes to prepare alkylated derivatives of ergothioneine of the structure in Formula (II):

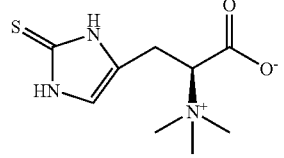

Formula (II)

wherein R and $R_1$ are independently alkyl, cycloalkyl, haloalkyl, cyanoalkyl or aralkyl.

Most preferred is the structure where $R=R_1=$methyl. Also preferred are $R=H$ and $R_1=$methyl. Further preferred is the structure where R=methyl and $R_1=H$. In a highly preferred embodiment, the present invention is directed to the preparation of ergothioneine by the reaction sequence involving Bamberger cleavage of the imidazole ring of a histidine alkyl ester by means of reaction with benzoyl chloride. In another preferred embodiment, the present invention is directed to the preparation of ergothioneine by the reaction sequence involving Bamberger cleavage of the imidazole ring of a histidine alkyl ester with an aryl, aralkyl, alkenyl, and alkynyl or alkyl acid chloride. Another preferred embodiment the present invention is directed to the preparation of ergothioneine by the reaction sequence involving Bamberger cleavage of the imidazole ring of a histidine alkyl ester with an alkyl, alkenyl, or aralkyl chloroformate. Of the chloroformate groups, the most preferred is phenyl chloroformate. Also preferred is vinyl chloroformate.

In yet another preferred embodiment, the present invention is directed to the preparation of ergothioneine by the reaction sequence involving Bamberger cleavage of the imidazole ring of a histidine alkyl ester with an alkyl, alkenyl, or aralkyl pyrocarbonate. Of the pyrocarbonate groups the most preferred is diethyl pyrocarbonate. In still another preferred embodiment, the present invention is directed to the preparation of ergothioneine by the reaction sequence involving ring closure with stereochemical retention of configuration by means of reaction with potassium thiocyanate or another alkali metal or alkyl or aryl amine thiocyanate salt. In an additional preferred embodiment, the present invention is directed to the preparation of ergothioneine by means of reductive alkylation with a borohydride and an alkyl aldehyde of a suitably protected thiohistidine under conditions where stereochemical configuration and optical activity are maintained. In such a reaction, the initially formed eneamine is reduced to an amine by a mild reducing agent. The most preferred reducing agent is sodium triacetoxyborohydride.

Within the process, an N-alkyl histidine or an N,N'-dialkylhistidine may be employed. N-methylhistidine and N,N'-dimethylhistidine are commercially available as the hydrochloride salts. Other such derivatives may be readily prepared by one normally skilled in the art (see e.g. Reinhold, V. N. et al., *J. Med. Chem.* 11 (1968) pp. 258-60; Aurelio, L. et al., *J. Org. Chem.* 68 (2003) pp. 2652-67). Many of the starting materials are either commercially available or known in the literature and others can be prepared following literature methods described for analogous compounds. The skills required in carrying out the reaction and purification of the resulting reaction products are known to those in the art. Purification procedures include e.g., distillation, crystallization, and normal phase or reverse phase chromatography.

The following examples are provided for the purpose of further illustration only and are not intended to be limitations on the disclosed invention. All reagents were obtained from commercial suppliers and were used without further purification. ¹H NMR and ¹³C NMR were obtained from a JEOL Eclipse 270 spectrometer at room temperature at 270 MHz (¹H) and 67.5 MHz (¹³C). An Agilent 1200 HPLC system equipped with UV and mass detectors was used for in-process as well as final assays. Optical rotations were recorded using a Rudolph Research Autopol V polarimeter. Melting points were run in open tube capillaries and are uncorrected. Mass spectra were recorded on an Agilent 6100 Series Single Quadrupole LC/MS system.

EXAMPLE 1

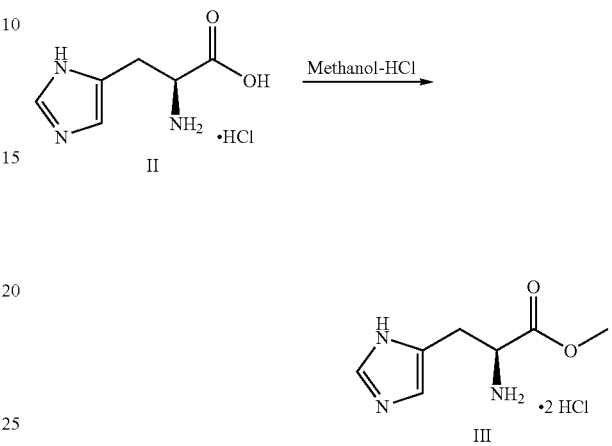

The methyl ester of histidine III was prepared by a modification of the method of Cook, Fujii, Tanaka and Tsuchiya (Cook et al., Antistaphylococcal and antifibrinolytic activities of .omega.-amino acids and their L-histidine dipeptides, *J. Med. Chem.*, 14 (1971) pp. 354-57). In a 200 L Schott glass kettle equipped with an air-driven stirrer, an efficient condenser, and inlet for gaseous introduction, is placed 12.5 Kg L-Histidine hydrochloride monohydrate, which is suspended in 130 L methanol (MeOH). Dry HCl gas is introduced. As the dry HCl is introduced the mixture is heated to a temperature range of 55-65° C. A solution is formed. Gaseous HCl introduction is continued to saturation and after reaching saturation, it is stopped. Soon after the solution is formed, a precipitate (product) starts to appear. The mixture is stirred; HCl gas occasionally further introduced (15 min every 1 hr); and the mixture is heated under low reflux for an 8-hour period. At the end of this time, it is allowed to stand an additional 6-8 hours. At the end of this time, a 40 L portion of ethyl acetate (EtOAc) is added, and the mixture is stirred for 1-hour period and filtered. The resultant filter cake is washed with 10 L of isopropyl ether and the resulting white crystalline product is air dried. Yield 95%. Mp 102-103° C. (Literature mp 102-103° C.). [α]²⁵D=+3.5° (c=2, H₂O). ¹H NMR (D₂O): δ 3.4 (t, 2 H), 3.9 (s, 3 H), 4.5 (s, 2 H), 7.4 (s, 1 H), 8.5 (s, 1 H).

EXAMPLE 2

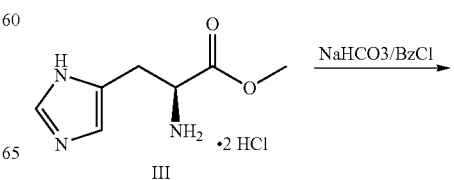

-continued

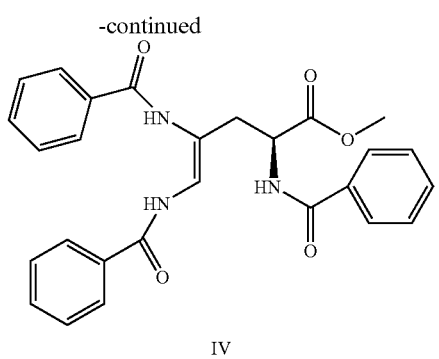

IV

A 100 liter Schott glass reactor equipped with an efficient air-powered stirrer and cooling coils is charged with 6.2 moles (1.5 Kg) of L-histidine methyl ester dihydrochloride in 20 L of a mixture of 10:90 tetrahydrofuran:distilled water. The solution is stirred and cooled to about 10° C. Then, 20 moles (7.9 equivalents, 4.1 Kg) of sodium bicarbonate is added with cooling. Then, a solution of 27 moles (3.3 L) of benzoyl chloride (4.35 equivalents) is added over a period of 30-60 minutes with efficient stirring at ambient temperature (RT). The resulting mixture is stirred for an 18-24 hour period. The organic layer is separated, washed with brine, dried (anhydrous magnesium sulfate) and filtered. The dry filtrate is placed in a Buchi rotary evaporator and evaporated under vacuum. The resultant oil is mixed with 20 L of diethyl ether and left at −10° C. overnight. The diethyl ether is decanted, solid residue is dissolved in 9 L of absolute ethanol, and mixed with 1 L triethylamine. The resulting solid is then treated with another 18 L portion of diethyl ether for an 18-24 hr period at −10° C. The resultant crystals are filtered and washed with a 2 L portion of ether and air dried. Yield 2.6 kg (88%). Mp 213-215° C. (Literature mp 219° C.). MS (ES$^+$) calcd for $C_{27}H_{25}N_3O_5$ 471.18 found 472.2 (M+1). $^1$H NMR (CDCl$_3$) δ.

EXAMPLE 3

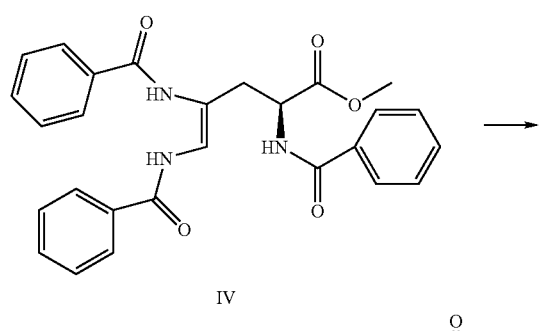

IV

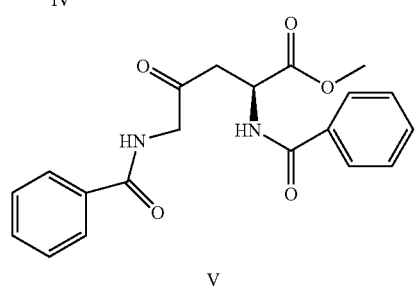

V

In a 100 L Schott glass reactor, 2.6 Kg (5.5 moles) of the tribenzoyl Bamberger intermediate (IV) is dissolved in 35 L of warm methanol containing 3.5 kg anhydrous HCl gas. A clear solution is achieved within a 30-60 minute period. The resultant solution is concentrated on a 50 L Buchi rotary evaporator to a volume of approximately 3-3.5 L. The oily residue is mixed with 10 L of diethyl ether and 33 L of ice-water and left at 0-5° C. overnight. Crystals are formed, which are washed with a 2 L portion of water and then with 1 L of diethyl ether and air dried. Yield 1.6 kg (79%). Mp 156-158° C. (Literature mp 158° C.). MS (ES$^+$) calcd for $C_{20}H_{20}N_2O_5$ 368.14 found 368.1 (M+1). $^1$H NMR (CDCl$_3$) δ 3.2 (t, 2 H), 3.75 (s, 3 H), 4.3 (d, 2H), 5.05 (m, 1 H), 7.4-7.6 (m, 6 H), 7.8 (d, 4 H).

EXAMPLE 4

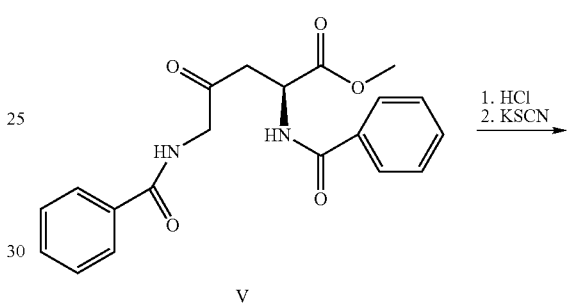

V

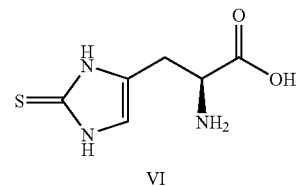

VI

In a 100 L Schott glass reactor with heating coils and stirring, is placed 4.32 moles (1.6 Kg) of ketodibenzamide (V). This is then dissolved in 10 L of conc. HCl and 8.2 L water. The resulting solution is stirred under thermostatically-controlled heating at 90-93° C. for a 15-hour period, whereupon it is cooled to 1-5° C. The resulting crystals (benzoic acid) are filtered, and are washed with a 2.5 L portion of cold (5° C.) water to remove occluded product. The resulting aqueous solution is evaporated at 60° C. under high vacuum. Then, a 3.7 L portion of water and 1.070 Kg (11 moles; 1.1 equivalents) of potassium thiocyanate (KSCN) is added, and the solution heated to 80-90° C. for a three-hour period. At the end of this time period, the solution was cooled and treated with 1.1 equivalents (0.902 Kg) of sodium acetate. The solution was kept at 5° C. overnight, and the resultant product VI was filtered, washed with 2 L of cold (5° C.) water and air dried. Yield 450 g (55%). [α]$^{25}$D=−9.5 (c=2, 1N HCl) Lit $[\alpha]^{25}D=-9.5$ (c=2, 1N HCl). MS (ES+) calcd for $C_6H_9N_3O_2S$ 187.04 found 188.0 (M+1) $^1H$ NMR ($D_2O$) δ $^{13}C$ NMR ($D_2O$) δ.

EXAMPLE 5

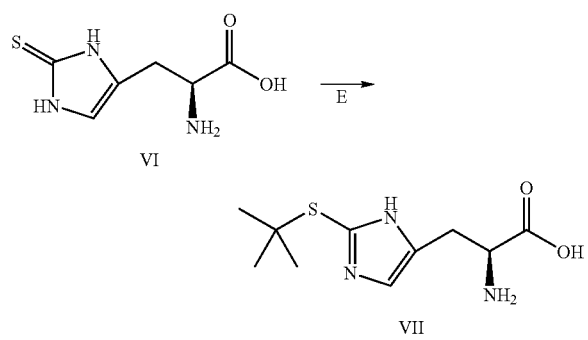

In a 3-neck, mechanically stirred, 5 L round bottom flask equipped with a heating mantle, 215 grams Thiohistidine (VI) was added into 1.7 L distilled water, immediately followed by the addition of 222 g tertiary-butanol and 340 mL concentrated 37% hydrochloric acid. The resulting mixture was heated to 85-90° C. (slight reflux) and kept at this temperature for a 3-hour period. NMR analysis showed complete conversion to the tertiary-butyl thioether at this time. The reaction mixture was worked up by concentrating under high vacuum on the rotary evaporator. The oily residue was co-evaporated twice with 100 mL portions of distilled water. Yield was 100% as dihydrochloride. Free amino acid is liberated by adjusting pH of the solution in the last evaporative step to 5.0 with aqueous sodium acetate, evaporation in vacuo to dryness, and extraction of the amino acid into warm 2-propanol. $[\alpha]^{25}D=+13°$ (c=1, $H_2O$). MS (ES+) calcd for $C_{10}H_{17}N_3O_2S$ 243.10 found 244.1 (M+1). $^1H$ NMR ($D_2O$), δ 1.3 (s, 9 H), 3.35 (d, 2 H), 4.2 (t, 2 H), 7.5 (s, 1 H). $^{13}C$ NMR ($D_2O$) δ 26.5, 30.2, 52.1, 52.7, 121.1, 129.6, 137.5, 170.7.

EXAMPLE 6

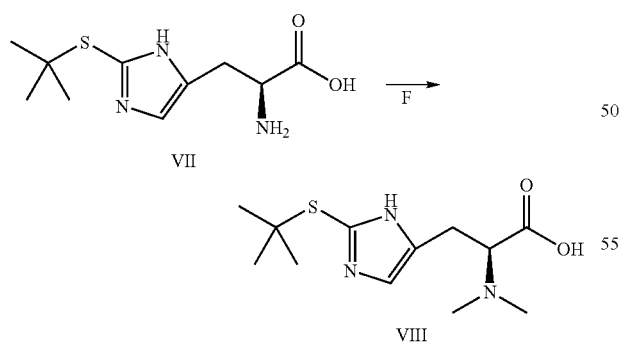

Into a mixture of 250 g (1 mole) of VII (amino acid base) in 3 L of tetrahydrofuran (THF), 325 g (2.9 equivalents) of commercial 37% formalin is added in one portion, followed by portionwise addition of 600 g (2.9 eq) of sodium triacetoxyborohydride at an internal temperature of 0-5° C. The resulting suspension is stirred at 10° C. for 6-8 hours. The reaction mixture is cooled to −10° C. and acidified with 2N HCl to pH<1. This solution is then evaporated under high vacuum on a Buchi rotary evaporator dryness at 45-50° C. bath temperature. The resulting residue is mixed with a 2 L portion methanol, and the undesired inorganic salts are filtered, and the filtrate is evaporated to dryness to yield the dihydrochloride salt of VIII. The free amino acid is liberated by triturating with aqueous sodium acetate to pH 5.0, evaporation to dryness, and extraction into 2-propanol, from which it can be recrystallized. Yield 95%. $[\alpha]^{25}D=+50°$ (c=1, $H_2O$). MS (ES+) calcd for $C_{12}H_{21}N_3O_2S$ 271.14 found 272.1 (M+1). 1H NMR ($D_2O$) δ 1.3 (s, 9 H), 2.9 (s, 6 H), 3.35-3.45 (m, 2 H), 4.1 (dd, 1 H), 7.5 (s, 1 H). $^{13}C$ NMR ($D_2O$) δ 23.1, 30.4, 41.5, 41.8, 49.0, 68.5, 120.7, 130.2, 137.1, 170.2.

EXAMPLE 7

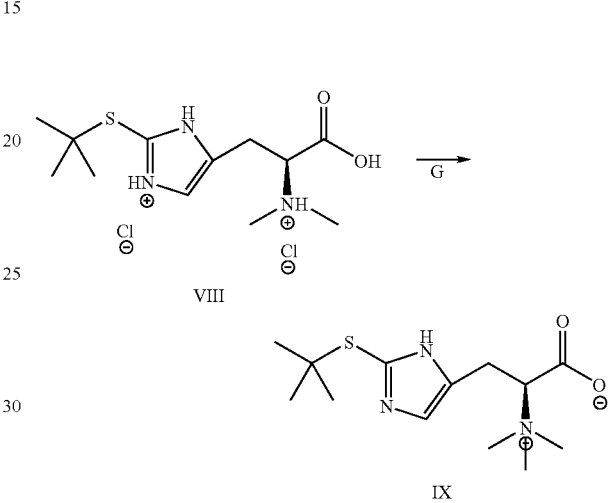

VIII is dissolved in methanol and adjusted to pH 8.8-9.0 with ammonium hydroxide. Iodomethane (1.5 eq.) is added and the solution is kept 24 hours at ambient temperature (RT). The mixture is concentrated; white solid (ammonium chloride) is filtered, cake washed with methanol and the combined filtrates are evaporated to dryness. The product is used directly for S-t-butyl deprotection. MS (ES+) calcd for $C_{13}H_{23}N_3O_2S$ 285.15 found 286.1 (M+1). $^1H$ NMR ($D_2O$) δ 1.3 (s, 9 H), 3.2 (m, 2 H), 3.3 (s, 9 H), 3.9 (dd, 1 H), 7.15 (s, 1 H). $^{13}C$ NMR ($D_2O$) δ

EXAMPLE 8

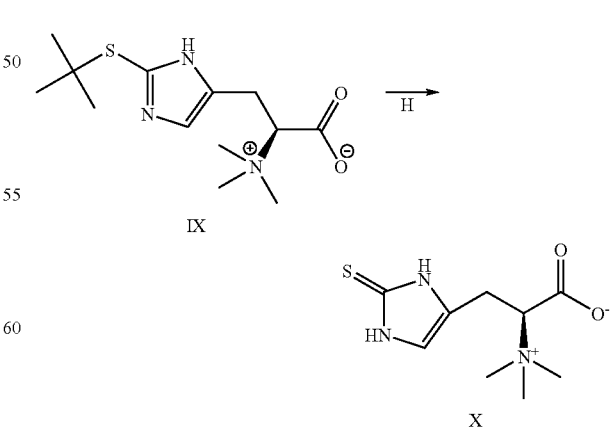

In a 100 L Schott glass kettle equipped with a heating jacket, efficient reflux condenser, and connection to vacuum, was placed a mixture of 34.3 L (40 equivalents) of concentrated (37%) hydrochloric acid and 21.2 Kg (20 equivalents) of 2-mercaptopropionic acid. Ten moles (2.85 Kg) of the quaternary inner salt (IX) was dissolved into the mixture, and the reaction mixture was heated under reflux for an 18-hour period. At the end of this time, the excess HCl was distilled off under reduced pressure. The residue was treated with 3×6 L portions of 50:50 (v/v) distilled water-ethyl acetate. The aqueous phase was retained and the organic phase discarded or retained for recycling. The combined aqueous layers were again extracted with 2×6 L portions of with ethyl acetate, the aqueous phase retained and the organic phase discarded. The aqueous phase was adjusted to pH 7 with 15% (w/v) ammonium hydroxide solution with cooling, and was evaporated on a Buchi rotary evaporator under high vacuum and 60° C. The solid residue was stirred with treated with absolute ethyl alcohol at room temperature for a 12-hour period. The slurry was then filtered on a sintered-glass Buchner funnel to give crude ergothioneine. Further purification could be achieved by recrystallization from aqueous ethanol, filtration as above, washing with acetone and dried in high vacuum at 40-50° C. This material matched the physical data of reference standard L-(+)-Ergothioneine (Sigma Chemical Co., St. Louis, Mo.) in all respects. Yield 62%. $[\alpha]^{25}D=+125°$ (c=1, $H_2O$). MS (ES+) calcd for $C_9H_{15}N_3O_2S$ 229.09 found 230.09 (M+1), Calcd for $C_9H_{15}N_3O_2S$: C, 47.14; H, 6.59; N, 18.33; O, 13.96; S, 13.98. Found: C, 47.18; H, 6.58; N, 18.30; O, 14.01; 13.96. $^1H$ NMR ($D_2O$) δ 3.2 (m, 2 H), 3.3 (s, 9 H), 3.9 (dd, 1 H), 6.8 (s, 1 H). $^{13}C$ NMR ($D_2O$) δ 23.0, 52.3, 77.2, 115.4, 123.9, 156.1, 170.2; uv max (water): 258 nm (ε 16000).

What is claimed is:

1. A process for preparing the compounds of Formula (I):

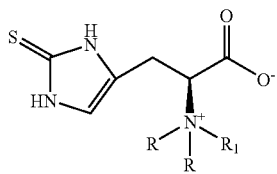

I wherein R and $R_1$ are independently chosen from hydrogen, $C_1$-$C_8$ alkyl, $C_3$-$C_8$ alkenyl, $C_3$-$C_8$ alkynyl, $C_3$-$C_7$ cycloalkyl, cycloalkyl-lower alkyl aryl-lower alkyl or substituted aryl-lower alkyl; comprising the following successive steps:
 a) reacting L-histidine alkyl ester with an acid halide, chloroformate or pyrocarbonate in the presence of a base thereby obtaining an alkyl-(S,Z)-2,4,5 triamidopent-4-enoate;
 b) hydrolysis of the alkyl-(S,Z)-2,4,5-triamidopent-4-enoate to obtain a (S)-alkyl 2,5-diamido-4-oxopentanoate;
 c) acid catalyzed hydrolysis of the (S)-alkyl 2,5-diamido-4-oxopentanoate followed by reaction with a metal thiocyanate to obtain a thiohistidine, (S)-2-amino-3-(2-thioxo-2,3-dihydro-1H-imidazol-4-yl)propanoic acid;
 d) protection of the sulfur of the thiohistidine by the addition of tert-butyl protecting group to obtain (S)-2-amino-3-(2-(tert-butylthio)-1H-imidazol-5-yl)propanoic acid;
 e) dialkylation of the primary amine to obtain a tertiary amine (S)-3-(2-(tert-butylthio)-1H-imidazol-5-yl)-2-(dialkylamino)propanoic acid;
 f) quaternization of the tertiary amine; and
 g) removal of the protecting group to obtain the desired (S)-3-(2-mercapto-1H-imidazol-5-yl)-2-(trialkylammonio)propanoate (I).

2. A process according to claim 1, wherein the above mentioned L-histidine alkyl ester is L-histidine methyl ester.

3. A process according to claim 1 wherein the above mentioned acid halide is benzoyl chloride.

4. A process according to claim 1 wherein the hydrolysis of the alkyl-(S,Z)-2,4,5-triamidopent-4-enoate is carried out in methanol containing anhydrous hydrogen chloride gas.

5. A process according to claim 1 wherein the acid catalyzed hydrolysis of the (S)-alkyl 2,5-diamido-4-oxopentanoate is carried out using concentrated hydrochloric acid and water.

6. A process according to claim 1, wherein the above mentioned metal isothiocyanate is potassium or sodium isothiocyanate.

7. A process according to claim 1, wherein the thiohistidine is protected using water, tertiary butanol and hydrochloric acid.

8. A process according to claim 1, wherein the dialkylation of the tert-butyl protected thiohistidine is carried out using an aldehyde and triacetoxyborohydride.

9. A process according to claim 8 wherein the reaction is carried out at less than 15° C.

10. A process according to claim 1, wherein the quaternization of the S-tert-butyl-N,N-dialkyl thiohistidine is carried out at a pH range of from about 8.6 to about 9.2.

11. A process according to claim 1, wherein the quaternization of the S-tert-butyl-N,N-dialkyl thiohistidine is carried out using an alkyl, alkenyl, alkynyl or arylalkyl halide, alkylsulfonate, haloalkylsulfonate, arylsulfonate or substituted arylsulfonate.

12. A process according to claim 1, wherein the removal of the tert-butyl protecting group is carried out using hydrochloric acid in the presence of a scavenger of the tert-butyl cation.

13. A process for preparing (S)-3-(2-mercapto-1H-imidazol-5-yl)-2-(trimethylammonio)propanoate, known as L-ergothioniene, of Formula II:

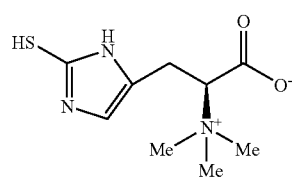

II comprising the following successive steps:
 a) reacting L-histidine alkyl ester with benzoyl chloride in the presence of a base thereby obtaining an alkyl-(S,Z)-2,4,5-triamidopent-4-enoate;
 b) hydrolysis of the alkyl-(S,Z)-2,4,5-triamidopent-4-enoate to obtain a (S)-alkyl 2,5-dibenzamido-4-oxopentanoate;
 c) acid catalyzed hydrolysis of the (S)-alkyl 2,5-dibenzamido-4-oxopentanoate followed by reaction with a potassium thiocyanate to obtain a thiohistidine, (S)-2-amino-3-(2-thioxo-2,3-dihydro-1H-imidazol-4-yl)propanoic acid;
 d) protection of the sulfur of the thiohistidine by the addition of a tert-butyl protecting group to obtain (S)-2-amino-3-(2-(tert-butylthio)-1H-imidazol-5-yl)propanoic acid;

e) dimethylation of the primary amine to obtain a tertiary amine (S)-3-(2-(tert-butylthio)-1H-imidazol-5-yl)-2-(dimethylamino)propanoic acid;

f) quaternization of the tertiary amine;

g) acid catalyzed removal of the protecting group to obtain the desired (S)-3-(2-mercapto-1H-imidazol-5-yl)-2-(trimethylammonio)propanoate (I).

14. A process according to claim 13, wherein the L-histidine alkyl ester is reacted with benzoyl chloride in the presence of a base; the base being selected from the group consisting of a carbonate, a bicarbonate, an amine or an alkylamine.

15. A process according to claim 13, wherein the above mentioned L-histidine alkyl ester is L-histidine methyl ester.

16. A process according to claim 13, wherein the dimethylation of the tert-butyl protected thiohistidine is carried out using formalin and triacetoxyborohydride.

17. A process according to claim 16 wherein the reaction is carried out at less than 10° C.

18. A process according to claim 13, wherein the quaternization of the S-tert-butyl-N,N-dimethyl thiohistidine is carried out at a pH range of from about 8.7 to about 9.1.

19. A process according to claim 13, wherein the quaternization of the S-tert-butyl-N,N-dimethyl thiohistidine is carried out using a methyl halide, methyl methanesulfonate, methyltoluenesulfonate, methylbenzenesulfonate, methyl trifluoromethanesulfonate or trimethyloxonium tetrafluoroborate.

20. A process according to claim 13, wherein the acid catalyzed removal of the tert-butyl protecting group is carried out using hydrochloric acid in the presence of a scavenger of the tert-butyl cation.

21. A process according to claim 12, wherein the removal of the tert-butyl protecting group is carried out using hydrochloric acid in the presence of 2-mercaptopropionic acid.

22. A process according to claim 20, wherein the acid catalyzed removal of the tert-butyl protecting group is carried out using hydrochloric acid in the presence of 2-mercaptopropionic acid or anisole.

\* \* \* \* \*